(12) United States Patent
Missbichler et al.

(10) Patent No.: US 8,003,343 B2
(45) Date of Patent: Aug. 23, 2011

(54) METHOD FOR DETERMINING DIAMINE OXIDASE

(75) Inventors: Albert Missbichler, Vienna (AT); Isabella Mayer, Klein Pochlam (AT)

(73) Assignee: Sciotec Diagnostic Technologies GmbH, Tulln (AT)

( * ) Notice: Subject to any disclaimer, the term of this patent is extended or adjusted under 35 U.S.C. 154(b) by 499 days.

(21) Appl. No.: 12/093,586

(22) PCT Filed: Nov. 17, 2006

(86) PCT No.: PCT/AT2006/000473
§ 371 (c)(1),
(2), (4) Date: May 13, 2008

(87) PCT Pub. No.: WO2007/056788
PCT Pub. Date: May 24, 2007

(65) Prior Publication Data
US 2008/0227116 A1 Sep. 18, 2008

(30) Foreign Application Priority Data

Nov. 18, 2005 (AT) ................ A 1881/2005

(51) Int. Cl.
*C12Q 1/26* (2006.01)
(52) U.S. Cl. .......................................... 435/25; 435/28
(58) Field of Classification Search ............... 435/25, 435/28
See application file for complete search history.

(56) References Cited

U.S. PATENT DOCUMENTS

| | | | | |
|---|---|---|---|---|
| 4,818,683 | A | 4/1989 | Morel et al. | 435/7.9 |
| 5,124,254 | A | 6/1992 | Hewlins et al. | 435/28 |
| 5,284,749 | A * | 2/1994 | Cowley et al. | 435/7.1 |
| 2005/0214894 | A1 * | 9/2005 | Schofield et al. | 435/25 |

FOREIGN PATENT DOCUMENTS

AT    411 688    4/2004

OTHER PUBLICATIONS

Van der Meer et al. Covalently Bound Pyrroloquinoline Quinone is the Organic Prosthetic Group in Human Placental Lysyl Oxidase. Biochem J 239 789-791, 1986.*
Van der Meer et al. Hydrazone Formation of 2,4-Dinitrophenylhydrazine with Pyrrologquinline Quinone in Porcine Kidney Diamine Oxdiase. FEBS 206(1)111-114, Sep. 1986.*
Garcia-Villar N. et al. Determination of Histamine in Wines with an Online Precolumn Flow Derivatization System Coupled to HPLC. Analyst 130 1286-1290, Jul. 2005.*
Oguri S. et al. Assay and Biological Relevance of Endogenous Histamine and its Metabolites. J of Chromatography B 781(2002)65-179.*
Agrawal V. et al. QSAR Studies on Acylated Histamine Derivatives. Bioorganic & Medicinal Chemistry 9(2001)2787-2792.*
Morel A. et al. Immunoanalytis of Histamine Through a Novel Chemical Derivatization. J Allergy Clin Immunol 82:646-654, 1988.*
Held, P. et al. Analysis of Histamine in Wine Samples Using the Microplate Format. BioTek Instruments Aug. 28, 2006.*
Garcia-Villar N. et al. Determination of Histamine in Wines with an On-Line Pre-Column Flow Derivatization System . . . The Analyst 2005, 130, 1286-1290.*
Agrawal and Khadikar, "QSAR studies on acylated histamine derivatives," *Bioorg. Med. Chem.*, 9:2787-2792, 2001.
Aygün et al., "Comparison of ELISA and HPLC for the determination of histamine in cheese," *J. Agric. Food Chem.*, 47:1961-4, 1999.
Bachrach, In: Mondovi (Ed.), *Structure and Functions of Amine Oxidase* Boca Raton: CRC Press, 5-20, 1985.
Bolygo et al., "Determination of histamine in tomatoes by liquid chromatography/mass spectrometry," *J. AOAC Int.*, 83:543-8, 2000.
Campbell et al., "Modulation of eicosanoid and histamine release from human dispersed lung cells by terfenadine," *Allergy*, 48:125-9, 1993.
Claret et al., "Homogeneous time resolved fluorescence assay to measure histamine release," *Comb. Chem. High. Throughput. Screen*, 6:789-94, 2003.
Elmore et al., "Human kidney diamine oxidase: heterologous expression, purification, and characterization," *J. Biol. Inorg. Chem.*, 7:565-679, 2002.
Garcia-Villar et al., "Determination of histamine in wines with an on-line pre-column flow derivatization system coupled to high performance liquid chromatography," *Analyst.*, 130:1286-1290, 2005.
Hibi and Senda, "Enzymatic assay of histamine by amperometric detection of H2O2 with a peroxidase-based sensor," *Biosci. Biotechnol. Biochem.*, 64:1963-1966, 2000.
Janes et al., "A new redox cofactor in eukaryotic enzymes: 6-hydroxydopa at the active site of bovine serum amine oxidase ," *Science*, 248:981-7, 1990.
Janes et al., "Identification of topaquinone and its consensus sequence in copper amine oxidases," *Biochemistry*, 31:12147-12154, 1992.
Kehoe et al., "Plasma diamine oxidase activity is greater in copper-adequate than copper-marginal or copper-deficient rats," *J. Nutr.*, 130:30-33, 2000.
Kitanaka et al., "Expression of diamine oxidase (histaminase) in guinea-pig tissues," *Eur. J. Pharmacol.*, 437:179-85, 2002.
Kluetz and Schmidt, "Diamine oxidase: molecular weight and subunit analysis," *Biochemical and Biophysical Research Communications*, 76:40-45, 1977.
Köhler and Milstein, "Continuous cultures of fused cells secreting antibody of predefined specificity," *Nature*, 256:495-7, 1975.

(Continued)

*Primary Examiner* — Ralph Gitomer
(74) *Attorney, Agent, or Firm* — Fulbright & Jaworski LLP

(57) ABSTRACT

Disclosed is a method for determining histaminase (DAO; EC 1.4.3.6) activity in a sample. Said method comprises the following steps: an aqueous solution is supplied which contains a predefined amount of a diamine; the aqueous solution is mixed and incubated with the sample for a given period of time in conditions in which the diamine can be reacted with a DAO possibly present in the sample; the diamine is derivatized; the amount of derivatized diamine is determined; the predefined amount of diamine is compared to the amount of derivatized diamine; and the activity of histaminase possibly present is determined.

17 Claims, 4 Drawing Sheets

OTHER PUBLICATIONS

Küfner et al., "Determination of histamine degradation capacity in extremely small human colon samples," *Inflamm. Res.*, 2:596-7, 2001.

Mayer et al., "Optimierter radioextraktionsassay zur quantitativen Bestimmung der Aktivität von Diaminooxidase (DAO) in humanem Serum und Plasma," *Allergologie*, 28:1-8, 2005.

Mizuguchi et al., "Purification and characterization of diamine oxidase (histaminase) from rat small intestine," *J. Biochem.*, 116:631-5, 1994.

Morel and Delaage, "Immunanalysis of histamine through a novel chemical derivatization," *The Journal of Allergy and Clinical Immunology*, 82:646-654, 1988.

Morel et al., "Recognition of imidazole and histamine derivatives by monoclonal antibodies," *Mol. Immunol.*, 27:995-1000, 1990.

Mu et al., "Tyrosine codon corresponds to topa quinone at the active site of copper amine oxidases," *J. Biol. Chem.*, 267:7979-82, 1992.

Nilsson et al., "Inhibition of diamine oxidase promotes uptake of putrescine from rat small intestine," *Inflamm. Res.*, 45:513-518, 1996.

Novotny et al., "Diamine oxidase is the amiloride-binding protein and is inhibited by amiloride analogues," *J. Biol. Chem.*, 269:9921-9925, 1994.

Oguri et al., "Direct detection of endogenous histamine in rat peritoneal mast cells by in-capillary derivatization high-performance capillary electrophoresis," *J. Chromatogr. B. Biomed. Sci. Appl.*, 736:263-71, 1999.

Pietrangeli et al., "Inactivation of copper-containing amine oxidases by turnover products," *Eur. J. Biochem.*, 271:146-152, 2004.

Previati et al., "Determination of histamine in the whole blood of colon cancer patients," *J. Chromatogr. B. Analyt. Technol. Biomed. Life Sci.*, 780:331-9, 2002.

Rinaldi et al., "Diamine oxidase from pig kidney: new purification method and amino acid composition," *Preparative Biochemistry*, 12:11-28, 1982.

Rinaldi et al., "Purification and properties of diamine oxidase from *Euphorbia* latex," *Eur. J. Biochem.*, 127:417-422, 1982.

Shah and Ali, "The glycoprotein nature of pig kidney diamine oxidase," *Biochem. J.*, 253:103-107, 1988.

Song et al., "Assay of histamine by nano-liquid chromatography/tandem mass spectrometry with a packed nanoelectrospray emitter," *Rapid Commun. Mass. Spectrom.*, 18:2818-22, 2004.

Taylor and Sumner, "Determing of histamine, putrescine, and cadaverine," *Seafood Quality Determination*, Elsevier Science Publishers, Amsterdam, 235-244, 1986.

Toyo'oka et al., "Hair analysis of histamine after fluorescence labeling by column-switching reversed-phase liquid chromatography with electrospray ionization mass spectrometry and application to human hair," *Anal. Biochem.*, 333:236-45, 2004.

Tufvesson and Tryding, "Determination of diamine oxidase activity in normal human blood serum," *Scand. J. Clin. Lab. Invest.*, 24:163-8, 1969.

Yoshida et al., "Simultaneous determination of histamine and histidine by liquid chromatography following intramolecular excimer-forming fluorescence derivatization with pyrene-labeling reagent," *Anal. Sci.*, 20:557-9, 2004.

Yoshitake et al., "A sensitive and selective determination method of histamine by HPLC with intramolecular excimer-forming derivatization and fluorescence detection," *Biomed. Chromatogr.*, 17:509-16, 2003.

Yoshitake et al., "Determination of histamine in microdialysis samples from rat brain by microbore column liquid chromatography following intramolecular excimer-forming derivatization with pyrene-labeling reagent," *J. Neurosci. Methods*, 127:11-17, 2003.

Zhang and Sun, "Determination of histamine and histidine by capillary zone electrophoresis with pre-column naphthalene-2,3-dicarboxaldehyde derivatization and fluorescence detection," *J. Chromatogr. A.*, 1040:133-40, 2004.

* cited by examiner

METHOD FOR DETERMINING DIAMINE OXIDASE

This application is a national phase application under 35 U.S.C. §371 of International Application No. PCT/AT2006/000473 filed 17 Nov. 2006, which claims priority to Austrian Application No. A 1881/2005 filed 18 Nov. 2005. The entire text of each of the above-referenced disclosures is specifically incorporated herein by reference without disclaimer.

The invention relates to a method for determining the activity of diamine oxidase (DAO; EC 1.4.3.6).

Histamine (1H-imidazole-4-ethylamine) is formed by the enzymatic decarboxylation of histidine and is, thus, a basic biogenic amine having a molecular weight of 111 Da.

Histamine is practically ubiquitarily present in the organism. It is produced by humans themselves and stored in the metachromatic granules of the mast cells and basophilic leucocytes, where it is available for immediate release. The highest histamine concentrations are measured in the lung. Upon release, histamine is an extremely potent mediator of a plurality of physiologic and pathophysiologic processes, frequently also by its interaction with cytokines.

In addition, histamine may also enter the body from outside, either by breathing in or, for instance, orally by the ingestion of histamine-containing foods such as cheese, wine, fish preservatives and sauerkraut.

The most important functions and effects of histamine in human and animal bodies include:
1. Capillary dilatation, increase in the capillary permeability and drop of blood pressure.
2. Contractions of the smooth muscles, i.a., of the bronchial muscles in the lung.
3. Induction of an elevated gastric acid secretion.
4. Increase in the heart frequency.
5. Histamine is the mediator of immediate-type allergic reactions, it is the most important mediator of allergic diseases such as $Rhinitis\ allergica$ (hay fever) and $Asthma\ bronchiale$.
6. Moreover, histamine is the classic trigger of urticaria (nettle rash) and plays an important role in drug allergies or incompatibilities.

Elevated concentrations of free histamine in blood circulation on the one hand, or in the intestinal lumen on the other hand, cause undesired effects such as headache, a stuffed or runny nose, respiratory obstruction, tachycardia and extrasystoles, furthermore gastrointestinal symptoms eventually leading to soft faeces and, finally, diarrhea, as well as hypotension. Frequently, eyelid swellings and, sometimes, urticarial exanthema are also described. Moreover, reddening of the skin, blood pressure drops and bronchospasms may also occur.

In the organisms of mammals, histamine is degraded by two enzymes: diamine oxidase (DAO, EC 1.4.3.6) and histamine-N-methyltransferase (NMT, EC 2.1.1.8) (Mizuguchi et al. 1994). DAO catalyzes the oxidative deamination of histamine to imidazole acetaldehyde; NMT catalyzes the N-methylation to N-methyl-histamine.

Both degradation paths are essential to the organism: DAO eliminates histamine taken up by the gastrointestinal tract, for instance, via food; NMT controls the histaminergic signal transmission in the nervous system (Kitanaka et al., 2002).

The main task of DAO is to prevent that histamine taken in via food reaches the blood circulation from the intestines, or is directly taken up into the vegetative nervous system. If this protection mechanism fails, an anaphylactic shock may occur in the extreme case (Taylor 1986, Nilsson et al., 1996). DAO is a secretory protein and, therefore, functions extracellularly, whereas N-methyltransferase is merely active in the cytosol (Kufner et al., 2001).

Native DAO, which is able to degrade other biogenic amines such as, e.g., putrescine, spermidine and cadaverine besides histamine, and which is, for instance, obtained from pig's kidney, is a homodimeric copper-containing glycoprotein in which the subunits are linked by disulfide bridges. DAO has a molecular weight of about 182 kDA (Kluetz and Schmidt 1997, Rinaldi et al, 1982) and a carbohydrate portion of about 11% (Shah and Ali, 1988). This enzyme belongs to the class of copper-containing amine oxidases, which catalyze the oxidative deamination of primary amines to aldehydes, ammonia and hydrogen peroxide according to the following, general reaction scheme (Bachrach 1985): $RCH_2NH_2 + H_2O + O_2 \Rightarrow RCHO + NH_3 + H_2O_2$, wherein the residue R contains an amino group.

Characteristic of copper-containing amine oxidases is a topaquinone in the active center, which is formed by the post-translational modification of a preserved tyrosine residue (James et al., 1990, James et al., 1992, Mu et al., 1992).

DAO is above all encountered in the small intestine, in the liver, in the kidneys and in blood, in white blood cells. In pregnant women, DAO is additionally formed in the placenta. Pregnants have blood DAO-levels which are about 500 to 1000 times higher than those of non-pregnants.

DAO is continuously produced and excreted into the intestinal lumen. In healthy persons, histamine-rich food is, therefore, largely freed from histamine already in the intestine. The remaining histamine is degraded during its passage through the intestinal mucosa by the DAO seated there. Histamine is decomposed into imidazole acetaldehyde and, furthermore, into imidazole acetic acid. The cofactors of diamine oxidase are 6-hydroxydopa and, presumably, pyridoxal phosphate, i.e. vitamin B6. Diamine oxidase is a sensitive enzyme which can be inhibited by various substances such as other biogenic amines, alcohol and its degradation product acetaldehyde as well as various drugs.

As already mentioned before, exogenous histamine taken in via food, but also histamine produced naturally in the body, can trigger a variety of disorders due to allergic reactions. In terms of clinical significance, at least three forms of histamine intolerance based on reduced diamine oxidase activity are to be mentioned in particular:

Few humans suffer from congenital DAO deficiency and will not lose the same, either.

During an infection of the intestinal mucosa, a temporary DAO deficiency may occur. After the infection is gone, the DAO activity will normalize too.

In the context of the administration of various activity-inhibiting substances, an exogenously mediated, reduced CAO activity may occur. These include, above all, alcohol and its degradation product acetaldehyde, certain amine-rich foods and many drugs.

In all cases, the initially described symptoms will occur more or less massively and, in most cases, are hard to categorize. Rapid clarification of the functional activity of the enzyme will enable rapid and simple therapies and the design of appropriate diets.

U.S. Pat. No. 5,284,749 discloses a method for determining diamine oxidase in a sample, which uses antibodies for determining said diamine oxidase. The method described in the US document, in particular, serves to differentiate between diamine oxidase from amniotic fluid and diamine oxidase from serum.

U.S. Pat. No. 5,124,254 describes a method for detecting putrescine and cadaverine, in which a sample is reacted with diamine oxidase and the hydrogen peroxide formed thereby is detected by the aid of a further reaction, which causes coloration.

The methodology of the detection of the enzymatic activity in plasma is based on the property of DAO to catalyze the oxidation of diamines like histamine, putrescine (1,4-butane diamine) and cadaverine (1,5-pentane diamine).

A widely used standard technique for determining DAO activity is based on the reaction of $^{14}C$-labelled putrescine or cadaverine with DAO. The monoaldehyde formed thereby intra-molecularly cyclisizes with the amino group and can be extracted with, e.g., chloroform ($CHCl_3$) due to its poorer solubility in water. After this, the determination of the activity is effected through liquid scintillation counting (Tufvesson G; Tryding N: "Determination of diamine oxidase activity in normal human blood serum", Scand J Clin Lab Invest 1969 September; 24(2):163-8(ISSN: 0036-5513)).

This methodology, although almost universally applied, involves essential weaknesses, which have so far blocked any further spreading of the application of this principle: The reagents used, for instance, are to be classified as noxious or harmful. In order to improve extraction yields, chloroform (mutagenic, cancerogenic) has been replaced with toluene (harmful, highly inflammable, reprotoxic, fruit-damaging) in a presently applied method. That reagent too is, therefore, not generally recognized as safe. In addition, the mixture of plasma and toluene must be frozen in order to enable an acceptable separation of the then solid plasma phase from the liquid toluene phase. Furthermore, also the reactivity of the enzyme is relatively weak such that at least 250 µl sample must be used, which entails an accordingly large amount of extraction agent.

Another method for determining the enzymatic activity of DAO is disclosed in AT 411688. The method described therein requires the initial reaction of an aqueous solution of a defined amount of a diamine (e.g. histamine, putrescine, cadaverine) which cyclisizes intramolecularly, after one of the amine groups of DAO has been converted into an aldehyde group, wherein the cyclisized molecule exhibits a higher solubility in ethyl acetate than the non-cyclisized diamine, with DAO, whereby one of the amino groups is oxidized to an aldehyde group and said aldehyde group intramolecularly cyclisizes with the second amine group. The cyclisized product is subsequently extracted with ethyl acetate and detected. The diamine is preferably labelled radioactively, in particular with $^{13}C$ or $^{14}C$, or with a dye or a chromogenic group and, in particular, a fluorescent dye or a fluorogen.

In the scientific literature, methods for determining DAO activity by measuring the hydrogen peroxide produced in the DAO-catalyzed reaction of diamine with water and oxygen are, furthermore, described. In Kohoe C A et al. (J Nutr (2000) 130:30-33), for instance, the DAO activity is determined by the reaction of cadaverine dihydrochloride. The hydrogen peroxide formed in the reaction of DAO with cadaverine is subsequently supplemented with the sodium salt of 10-(carboxymethylamino-carbonyl)-3,7-bis-(dimethylamino)-phenothiazine, ascorbate oxidase and horseradish peroxidase, whereupon methylene blue is formed as a function of the amount of hydrogen peroxide formed. The amount of formed methylene blue is photometrically determined. Alternatively to this method, the formed hydrogen peroxide can also be determined amperometrically (cf., e.g., Hibi T. and Senda M., Biosci Biotechnol Biochem. (2000), 64:1963-1966). Since the stability of hydrogen peroxide in a solution is inter alia influenced by the temperature and by the presence of other compounds (the presence of metal ions, for instance, promotes the catalytic decomposition of the hydrogen peroxide by the hydrogen peroxide oxidizing the metal ions via radical intermediaries), the determination of the DAO activity by the hydrogen peroxide formation rate is suitable only with some reservation. In the absence of oxidizable substances, hydrogen peroxide will decompose autocatalytically, in particular at higher temperatures and at alkalinity, with the active oxygen reacting to molecular oxygen.

It is, thus, the object of the present invention to provide a method for determining DAO activity in a sample, which overcomes the drawbacks of the prior art described in the beginning. Especially the use of radioactively labelled substrates (such as, e.g., histamine, putrescine) and the measurement of formed hydrogen peroxide, which takes place to an unsatisfactory degree, are to be avoided. Since the use of radioactive material is only possible in specially equipped laboratories and the realization of a liquid extraction of cyclisized putrescine or cadaverine is, moreover, very labor-intensive, methods requiring radioactive substances or methods relying on liquid extraction are not very suitable for routine operation, for instance in hospitals. Furthermore, the disposal of radioactive materials and organic solvents is not unproblematic and, to some extent, cost-intensive.

The present invention, therefore, relates to a method for determining the activity of diamine oxidase (DAO; EC 1.4.3.6) in a sample, comprising the steps of:
providing a given amount of a diamine, preferably in an aqueous solution or lyophilized,
mixing and incubating the diamine with the sample for a fixed period under conditions at which the diamine can be reacted by a DAO possibly present in the sample,
derivatizing the still present diamine,
determining the amount of derivatized diamine, and
comparing the given amount of diamine with the amount of derivatized diamine and determining the activity of possibly present diamine oxidase.

The sample containing an amount of DAO to be determined, or supposed to contain DAO, may be blood (serum or plasma) from men or animals, tissues or tissue homogenates of human or animal origin, e.g. intestinal epithelial cells obtained by biopsy, cerebrospinal liquid, from a body liquid, a tissue sample, an in-vitro cell culture (both a bacterial, vegetable, animal, human cell culture or a culture of molds) or obtained from any other source. The samples may be used either directly or after one or several sample processing steps. Such sample processing steps will, for instance, depend on how the DAO is provided in the isolated samples. If the DAO is, for instance, contained in the cells of tissue sample or cell cultures, these must be opened prior the activity determination while preserving their enzymatic activities (e.g. by ultrasonic treatment, French Press, lysis reagents like detergents and enzymes, or homogenization). Furthermore, the sample to be examined may be admixed with reagents, salts and buffers, which will contribute to the stabilization of DAO. Sample matrices interfering with the activity determination of DAO or influencing the same in such a manner as to render impossible any significant statement on the amount of DAO actually contained in the sample should likewise be eliminated from the sample. The degradation of histamine is known to be preferably effected by DAO in the intestinal lumen and in the intestinal epithelial cells. A comparison of the activity of DAO in plasma and intestinal epithelial cells has demonstrated the hitherto postulated correlation. It is, moreover, noted that the activity of DAO is higher by a multiple (by a factor of about 100) in the intestinal epithelial cells than in blood.

The sample is contacted and mixed with the given amount of diamine preferably dissolved in an aqueous solution. It is, of course, also possible to directly add a given amount of diamine to a defined amount of sample (e.g. in crystal form). In doing so, a diamine amount is used which will not lead to a significant inhibition of DAO (DAO is, for instance, at least partially inhibited by the addition of at least 100 μM histamine, DAO is inhibited by about 60%, i.e. significantly, at a histamine concentration of about 500 μM. After having incubated this mixture for a fixed period during which the diamine contained in the aqueous solution is degraded in the presence of DAO as a function of the amount of the latter, the diamine remaining in the mixture is derivatized by 95%, preferably 99%, even more preferred 99.5%, in particular 100%. The incubation conditions must be selected such that the DAO possibly present in the sample is able to convert the present diamine. DAO is an enzyme which converts diamine substrates such as, e.g. histamine, at such reaction rates that the incubation time will preferably last for at least 30 minutes.

To enhance both specificity and sensitivity, a special configuration of the test system contemplates that the DAO is selectively enriched from the sample by the aid of a specific antibody bound to a solid phase. The reaction with histamine or other biogenic amines will then proceed without interfering influence by the sample matrix in a special buffer system promoting DAO activity. This buffer preferably comprises 10 to 200 mM, more preferably 20 to 100 mM, in particular 50 mM, Tris pH=8.5.

After the derivatization of the diamine, its portion in the mixture is determined. The measured amount of derivatized diamine is subsequently compared with the amount of diamine originally contained in the aqueous solution. The difference between the originally used amount of diamine and the amount of derivatized diamine measured after derivatization reflects the absolute amount of degraded diamine. The amount of diamine degraded within a defined period reflects the enzymatic activity in the sample, which is preferably expressed by units/ml (U/ml).

Since—as already pointed out in the beginning—DAO plays an important role in mammals and men, the method according to the invention can also be used to diagnose a histamine intolerance caused by a DAO deficiency or a reduced DAO activity. The method according to the invention is further suitable for monitoring a therapy for histamine intolerance. Healthy individuals will normally have DAO activities of >10 U/ml (cf., e.g., Mayer I et al. (2005) Allergologie 28:1-8). The method according to the invention enables the measurement of activities of as far as to below 3 U/ml. It is thereby possible to diagnose histamine intolerances in patients and/or monitor the treatment progress.

Due to the fact that the diamine is no longer accessible in the course of the derivatization of DAO, or is eliminated from the same, it is not necessary to add a DAO inhibitor to the reaction solution as mentioned below. An inhibitor may never-the-less be added in a preferred manner. The derivatization of the diamine thus fulfils several functions. On the one hand, the derivatization prevents further diamine from continuing to react with DAO after a defined period of time. On the other hand, the derivatization enables the detection of diamine present in the sample, free diamine being not accessible to quantification by means of binding partners such as antibodies.

By the additional admixture of a defined amount of DAO of known activity, the inhibition potential of a sample can be determined. It is, thus, feasible to find out whether a DAO deficiency exists in the sample to be investigated or, however, substances are present, which prevent a physiologically relevant effect of DAO. Such substances may either comprise high amounts of other biogenic amines such as, e.g., putrescine, cadaverine or spermine, which are preferably degraded by DAO relative to histamine, or were supplied to the body through drugs (known DAO inhibitors being, for instance, acetylcystein, ambroxol, aminophylline, amitriptylin, chloroquine, clavulanic acid, isoniazide, metamizole, metodoproamide and propafenone). By such preference, histamine is degraded either significantly more slowly or no longer at all, thus causing the symptoms described in the introductory part.

This configuration may further be used to test "inhibitor antagonists" and quantify their effects.

According to the invention, the diamine can be derivatized with a number of substances, the derivatized diamine being quantitatively and/or qualitatively determinable either directly (e.g. via a color reaction, by fluorescence) or indirectly (e.g. by the aid of antibodies or fragments thereof, derivative-specific binding partners). In this case, fluorescent groups may preferably be substituted on the diamine, which will also be used in chromatographic detection systems. Such groups may include: O-phthalaldehyde (OPA) (Oguri S et al. (1999) J Chromatogr B Biomed Sci Appl 736: 263-71; Previati M et al. (2002) J Chromatogr B Analyt Technol Biomed Life Sci 780: 331-9), 9-fluorenylmethylchloroformate (Aygun O et al. (1999) J Agric Food Chem 47: 1961-4), dansyl groups (Bolygo E et al. (2000) J AOAC Int 83: 543-8), allophycocyanine (XL 665) (Claret E J et al. (2003) Comb Chem High Throughput Screen 6: 789-94), pyrene (Yoshida H et al. (2004) Anal Sci 20: 557-9) (e.g. 4-1-pyrene butyric acid N-hydroxysuccinimide ester=PSE (Yoshitake T et al. (2003) Biomed Chromatogr 17: 509-16)), 7-fluoro-4-nitrobenzoxadiazole (NBD-F) (Song Y et al. (2004) Rapid Commun Mass Spectrom 18: 2818-22), 4-(N,N-dimethylaminosulfonyl)-7-fluoro-2,1,3-benzoxadiazole (DBD-F) (Toyooka T et al. (2004) Anal Biochem 333: 236-45), naphthalene-2,3-dicarboxaldehyde (NDA) (Zhang L Y and Sun M X (2004) J Chromatogr A 1040: 133-40). These substituents may, of course, also be determined by the aid of antibodies binding to the derivatized diamine. Succinyl glycinamide is used to derivatize diamine in radioimmunoassays (Morel A et al. (1990) Mol Immunol 27 (10): 995-1000).

A further aspect of the present invention relates to a method for identifying diamine oxidase inhibitors and for determining the inhibition capacities of said inhibitors, comprising the steps of:
 providing a given amount of a diamine, preferably in an aqueous solution or lyophilized, and of diamine oxidase,
 mixing and incubating the diamine and the diamine oxidase with a compound potentially inhibiting the activity of diamine oxidase, for a fixed period under conditions at which the diamine can be reacted by a DAO possibly present in the sample,
 derivatizing the still present diamine,
 determining the amount of derivatized diamine,
 comparing the given amount of diamine with the amount of derivatized diamine and determining the activity of diamine oxidase, and
 optionally identifying diamine oxidase inhibitors by comparing the diamine oxidase activities with and without the addition of an inhibitor, a diamine oxidase inhibitor being identified as such if the activity of diamine oxidase is lowered by at least 20% by the inhibitor.

The method according to the invention may also be used to identify inhibitors of diamine oxidase and determine their inhibition capacities. In accordance with the invention, inhibitor is meant to denote a compound, or a mixture of compounds, which is able to lower the activity of diamine oxidase by at least 20%, preferably at least 40%, even more preferred at least 50%. In this context, a measurement performed under the same conditions as the measurement in the presence of the inhibitor is taken as a reference for the activity of DAO, said DAO being of the same origin.

According to a preferred embodiment, the diamine is selected from the group consisting of histamine, putrescine, spermidine and cadaverine.

Substrates exhibiting high affinities for DAO and good reaction rates with DAO are to be considered as particularly suitable for use in the method according to the invention (cf., e.g., Elmore B O et al. (2002) J Biol Inorg Chem 7:565-679). Histamine, putrescine, spermidine and cadaverine are, therefore, particularly suitable for the determination of the DAO activity in a sample. Furthermore, these diamines can be derivatized in a simple manner by known methods.

The aqueous solution preferably comprises a Tris (Tris (hydroxymethyl)-aminomethane) buffer solution having a pH of 7 to 9.5, preferably 7.5 to 9, in particular 8 to 8.5.

The concentration of Tris in the buffer solution may be 10 mM to 1 M, in particular 50 mM to 1 M. The addition of NaCl at a concentration of 10 to 400 mM, preferably 50 to 300 mM, in particular 200 mM, to the buffer solution will have particularly positive effects on the DAO activity.

According to a further preferred embodiment, the aqueous solution contains a diamine in an amount of from 5 to 400 µM, preferably 10 to 200 µM, in particular 80 µM.

Within this concentration range, DAO will exhibit the reaction rate required for the method according to the invention, without significantly inhibiting DAO.

The incubation of the aqueous solution with the sample preferably takes place at a temperature of from 10 to 50° C., 10 to 40° C., 15 to 37° C., 25 to 40° C., 18 to 26° C., 30 to 37° C. or 38° C., or of from 34 to 38° C.

Within this temperature range, DAO will exhibit sufficient activity to be used in the method according to the invention.

The incubation of the aqueous solution with the sample preferably is effected for 30 min to 36 h, preferably 1 to 30 h, even more preferred 3 to 24 h, in particular 18 h.

The necessary incubation time will amongst others depend on the incubation temperature. The better this temperature is adapted to the optimum temperature of DAO, the more efficient the conversion reaction and the shorter the incubation time will be. At room temperature (18-26° C.), for instance, the incubation time may even comprise several (e.g. 6 or 12) hours. Human DAO from plasma, for instance, has an activity jump in the range between 24° C. and 28° C. (markedly reduced activity if cooler). The incubation time must, therefore, be significantly extended at temperatures of <16° C.

According to a preferred embodiment, the incubation of the aqueous solution with the sample, and hence the reaction of diamine with the DAO contained in the sample, is stopped before derivatizing with amino guanidine, preferably at a concentration of 1 mM to 10 µM, in particular 10 mM.

In order to substantially prevent or reduce any further reaction of DAO with the substrate after the incubation time, inhibitors may also be used according to the invention.

In accordance with the invention, any DAO inhibitor known in the prior art can, of course, be used besides amino guanidine (Novotny W F et al. (1994) J Biol Chem 269:9921-9925): acriflavine, diazepam, N-methyl-N-formylhydrazine, b-amino-propionitril, dimaprit, O-methylhydroxylamine, agmantine, ethanol (10%), pargyline, aldomet, furosemide, phenamil, amiloride, guanabenz, phenelzine, aminoguanidine, guanfacine, phenformine, amitryptiline, guanidine, phenyprazine, amodiaquine, haloperidole, promethiazine, anserine, hyamine 1622, propranolol, aziridinylalkylamine, hydroxychloroquine, B1 pyrimidine, hydroxylamine, quinacrine, burimamide, impromidine, semicarbazide, imidazole derivatives, thiamine, carnosine, iproniazide, thioridazine, chlorothiazide, isocarboxazide, tranylcypramine, chloropromazine, isoniazide, trimethoprime, cimetidine, metiamide, tryptamine, clonidine, metronidazole, tyramine, cyanide, nazlinine (alkaloid) and Nt-methylhistamine.

According to a preferred embodiment of the present invention, the method step of derivatizing comprises acylating.

According to the invention, acylation is meant to denote the binding of an acyl group (R) of an organic acid of the formula (R—COOH), or its radical (R—CO*) to the free amino group of histamine. Such methods are all known to the skilled artisan (Agrawal V K et al. (2001) Bioorg. Med. Chem. 9:2787-2792). A special type of acylation, for instance, is an acylation in which the organic acid is acetic acid.

According to the invention, it has turned out that methods for derivatizing diamines comprising at least one acylation step are particularly suitable. Furthermore, it is, in particular, possible to detect acylated diamines, and optionally determine their concentrations in a sample, in a simple and reproducible manner. Antibodies specifically directed against acylated diamines can thus, for instance, be produced and used in a specific detection method (cf., e.g., Campbell A M et al. (1993) Allergy 48:125-9).

Diamine is preferably acylated with NHS biotin.

According to the invention, it is, however, also possible to acylate diamine with a number of other substances (cf., e.g., Morel A M und Delaage M A (1989) J Allergy Clin Immunol. 82:646-654).

According to a preferred embodiment, the amount of derivatized diamine is determined by chromatography, in particular high-performance liquid chromatography (HPLC), electrophoresis, in particular capillary electrophoresis (CE), or immunoassay, in particular enzyme-linked immunosorbent assay (ELISA) or radioimmunoassay (RIA).

Derivatized diamine can be quantitatively determined by various methods, chromatographic, electrophoretic and immuno-chemical methods, in particular, having turned out to be especially suitable. The quantitative determination of molecules and, in particular, acylated diamine can be performed with any of the methods mentioned herein. All these methods are sufficiently known to the skilled artisan and may readily be adapted at little and, hence, reasonable expenditures to the quantification of a plurality of diamines derivatized with different substances (cf., e.g., Garcia-Villar N et al. (2005) Analyst 130:1286-1290; Yoshitake T et al. (2003) J Neurosci Methods 127:11-17).

In a particularly preferred manner, derivatized diamine is quantified by immunochemical procedures, such procedures allowing for routine application, e.g. in hospitals, without excessive apparative expenditures. ELISA and RIA are, above all, perfectly suited to the purpose of the invention. A prerequisite for the use of immunochemical procedures in the method according to the invention is the provision of an antibody which is capable of differentiating between derivatized diamine and non-derivatized diamine. Such antibodies can, for instance, be produced by the injection of derivatized diamine into animals (e.g. rabbits, sheep, mice) or any other method known to the skilled artisan (e.g., Köhler G. and Milstein C., Nature (1975) 256:495-7). In U.S. Pat. No. 4,818,683, the production of antibodies directed against acylated histamine is, for instance, described, wherein said antibodies can be used to determine histamine in a sample.

The immunochemical procedures and, in particular, ELISA may be realized both competitively and simply. It is, for instance, possible to coat a solid carrier, preferably the wells of micro-titer plates (including 96, 384 or more wells), with derivatized diamine. The thus coated wells can subsequently be contacted with a mixture of derivatized diamine produced from the conversion reaction of diamine with the sample optionally comprising DAO and subsequent derivatization, and a diamine-derivative-specific antibody. The diamine derivative bound within the well competes with the derivatized diamine obtained from the conversion reaction for the diamine-derivative-specific antibodies in the solution. During the incubation in the well, an equilibrium will adjust, with the amount of antibodies bound to the diamine derivative of the well being the larger the more diamine has been reacted with DAO. The antibodies bound to the diamine derivative in the well after a washing step can either be quantified by a color reaction using a further antibody, which is directed against the diamine-derivative-specific antibody and preferably enzyme-labelled (e.g. with horseradish peroxidase). The degraded amount of diamine can be concluded from a parallelly performed determination of a standard series. Or the diamine-derivative-specific antibody itself could be labelled with, e.g., an enzyme (such as horseradish peroxidase, alkaline phosphatase). Alternatively, it is possible to immobilize in the wells an antibody directed against the diamine derivative, wherein said antibody is able to bind both labelled (e.g. with enzymes) and unlabelled diamine derivative. When determining diamine not reacted by the sample, the former will compete with added labelled diamine derivative for the free antibody binding sites. The more unlabelled diamine derivative is present, the less labelled diamine derivative can bind to the well via the binding antibody. The determination of labelled antibodies or diamine derivative is effected by methods known to the skilled artisan. It is, furthermore, possible, for instance if NHS biotin is used for the derivatization of diamine, to provide a solid carrier with streptavidine. The streptavidine molecules immobilized to the solid carrier (e.g. the wells of a microtiter plate) will subsequently be able to specifically bind the biotin of the derivatized diamine. Diamine converted by DAO, thus, cannot be bound to the solid carrier. The derivatized diamine bound to the solid carrier via streptavidine can subsequently be directly or indirectly detected and optionally quantified by an antibody specifically directed against derivatized diamine. It goes without saying that streptavidine may be replaced with any other binding partner, provided the latter is able to bind derivatized diamine while, nevertheless, enabling the accessibility of antibodies specific for the derivatized diamine.

Basically, any method described in the literature may be used for detecting derivatized diamines and, in particular, diamine derivatives (cf., e.g., Claret E J et al. Comb Chem High Throughput Screen (2003) 6:789-94).

During derivatization, it is to be taken care that other substances in the sample, which comprise free amino groups, can be acylated as well. Therefore, a blank value should in any case be initially determined, on the one hand, and the method for determining the acylated diamine should be specific, on the other hand, wherein, for instance, a binding parter such as an antibody is used, which is substantially merely able to recognize the acylated diamine.

Diamine oxidase can partially also be inhibited by one of its reaction products, namely hydrogen peroxide (Pietrageli et al. (2004) Eur. J. Biochem. 271, 146-152). In order to prevent or reduce such an inhibition, peroxidase (EC 1.11.1), preferably catalase (EC 1.11.1.6), is admixed to the aqueous solution and/or the sample—as in correspondence with a preferred embodiment of the present invention.

According to a preferred embodiment, the peroxidase or catalase is admixed in an amount of from 0.1 to 10, preferably 0.2 to 5, even more preferred 0.5 to 2, in particular 1, unit(s) per 100 µl sample.

Another aspect of the present invention relates to a kit for the determination of the activity of diamine oxidase (DAO; EC 1.4.3.6) in a sample, which comprises:
a diamine derivatization reagent,
means for determining derivatized diamine,
optionally peroxidase, preferably catalase (preferably in lyophilized form),
optionally a stabilized DAO preparation,
optionally a DAO buffer, and
optionally a diamine as a substrate.

A kit as defined herein is particularly suitable for the determination of the activity of diamine oxidase in a sample, preferably by the method according to the invention. The derivatization reagent substantially comprises the chemicals, buffers and the like required for the derivatization of a diamine. As the most important and optionally single component of the derivatization reagent are to be regarded those reagents which are responsible for the derivatization of the diamine (e.g. acyl group donors). Furthermore, the kit may contain means for determining derivatized diamine. Such means preferably comprise antibodies directed against derivatized diamine, in particular polyclonal antibodies and optionally secondary antibodies, wherein at least one of these antibodies is preferably enzymatically or chemically labelled. The provided antibodies as a function of their use can be derived from the most diverse sources (e.g. from a cell culture, from an animal like a sheep, rabbit or mouse) and labelled (e.g. with an enzyme, with biotin, with streptavidine, with a radionucleid) or unlabelled.

To carry out a control reaction using a defined amount of DAO, the kit according to the invention may also contain a stabilized DAO preparation. Such a DAO preparation may, for instance, contain lyophilized or cold-stabilized DAO (suitable for storage at temperatures of between −30° C. and −10° C., or between 1° C. and 6° C., respectively).

Furthermore, the kit according to the invention may also comprise a DAO buffer which is, in particular, suitable for the determination of the activity of DAO. The DAO buffer may be provided in concentrated form (e.g., as a 5-, 10-, 20- or 50-fold concentrate) in the kit.

The kit according to the invention may also contain acylated diamine, which can be used as a standard in the determination of the enzymatic activity and, in particular, in the determination of the amount of derivatized diamine.

The present invention is further outlined by the following Figures and Examples, yet without being limited thereto.

Figure 5:
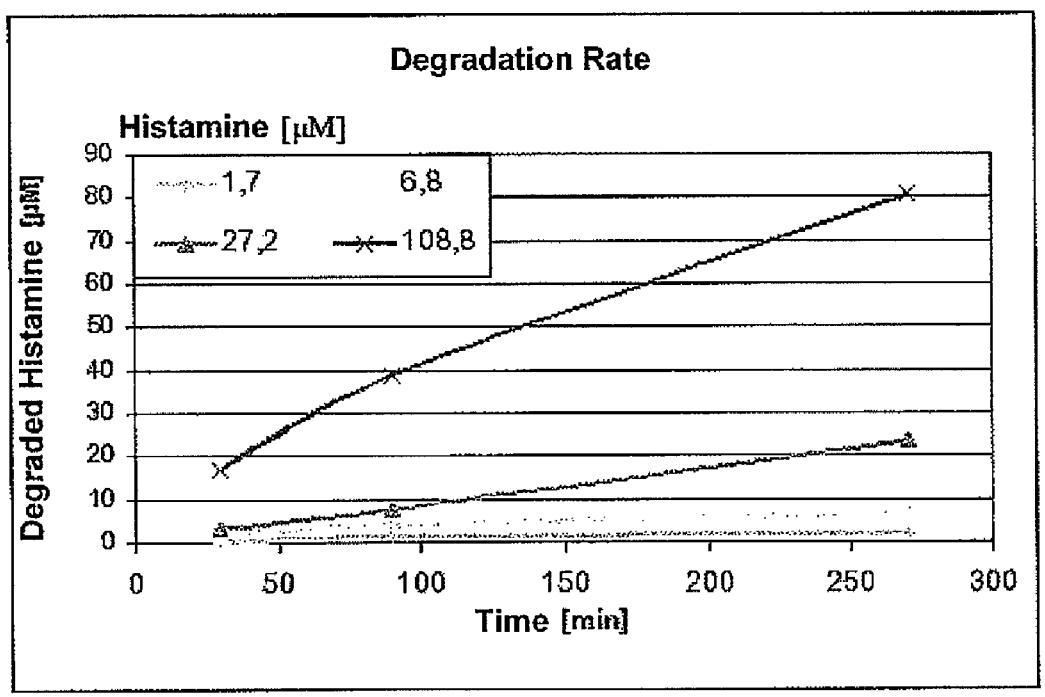

FIG. 5 illustrates the degradation rate of histamine at a DAO activity of 80 U/ml. According to the Michaelis-Menten characteristics of the enzyme, the conversion of histamine is a function of the concentration of the histamine used. This Figure indicates the conversion course for a DAO activity of 80 U/ml.

Figure 6:
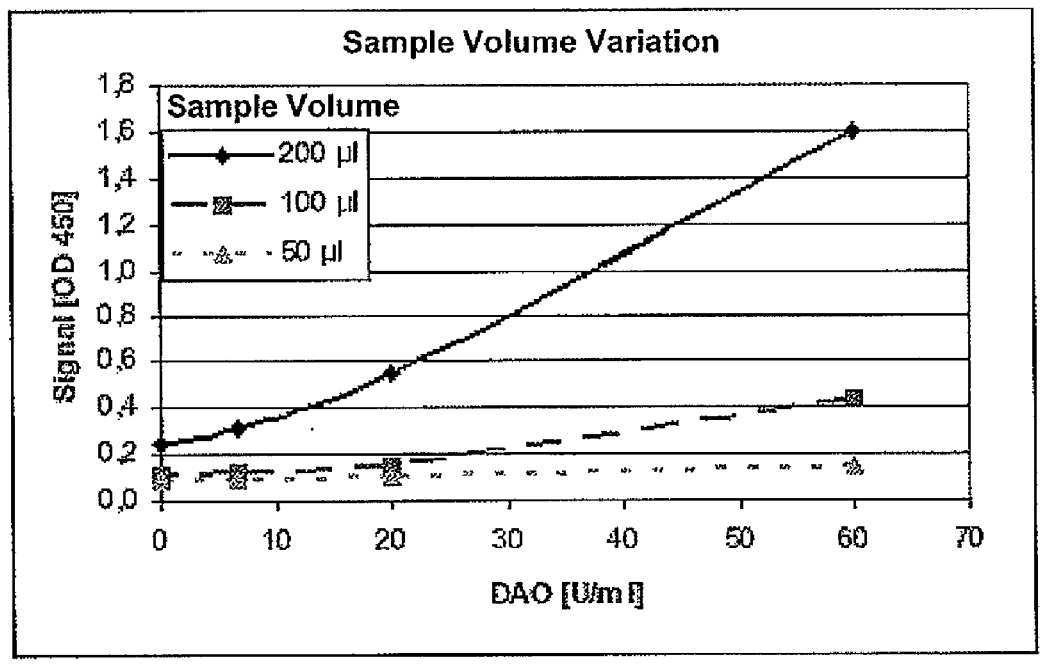

FIG. 6 shows the dependence of the sensitivity of the method according to the invention on the sample volume used.

Figure 7:
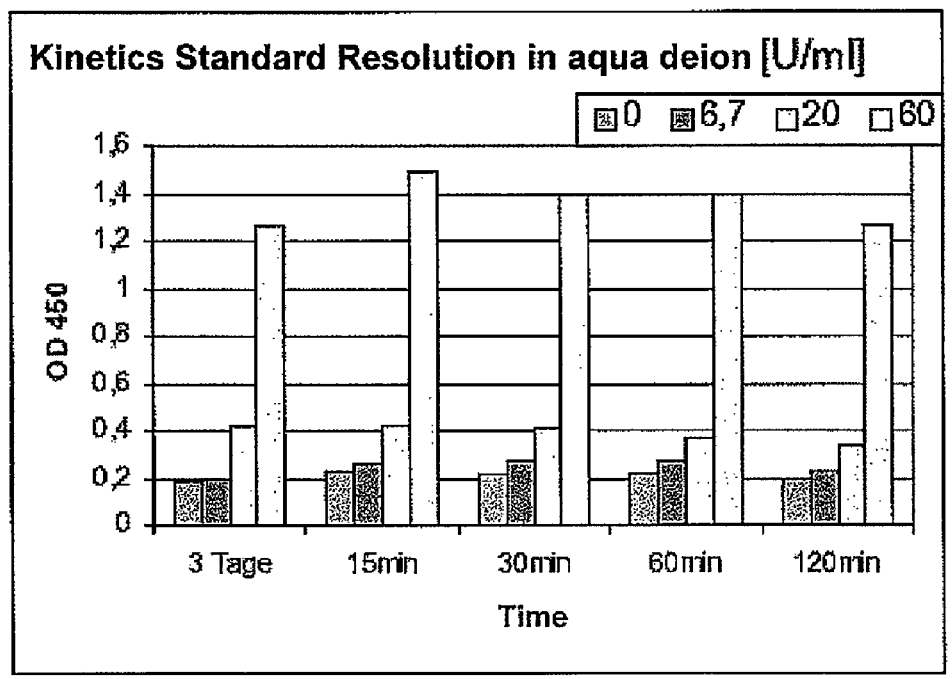

FIG. 7 illustrates the activity of DAO prepared from a lyophilisate. In order to ensure the optimum stability of the test system, DAO is prepared in lyophilized form for the standard curve. The overall activity is already available 15 min after resolution and will remain stable even after three days at room temperature.

Figure 8:
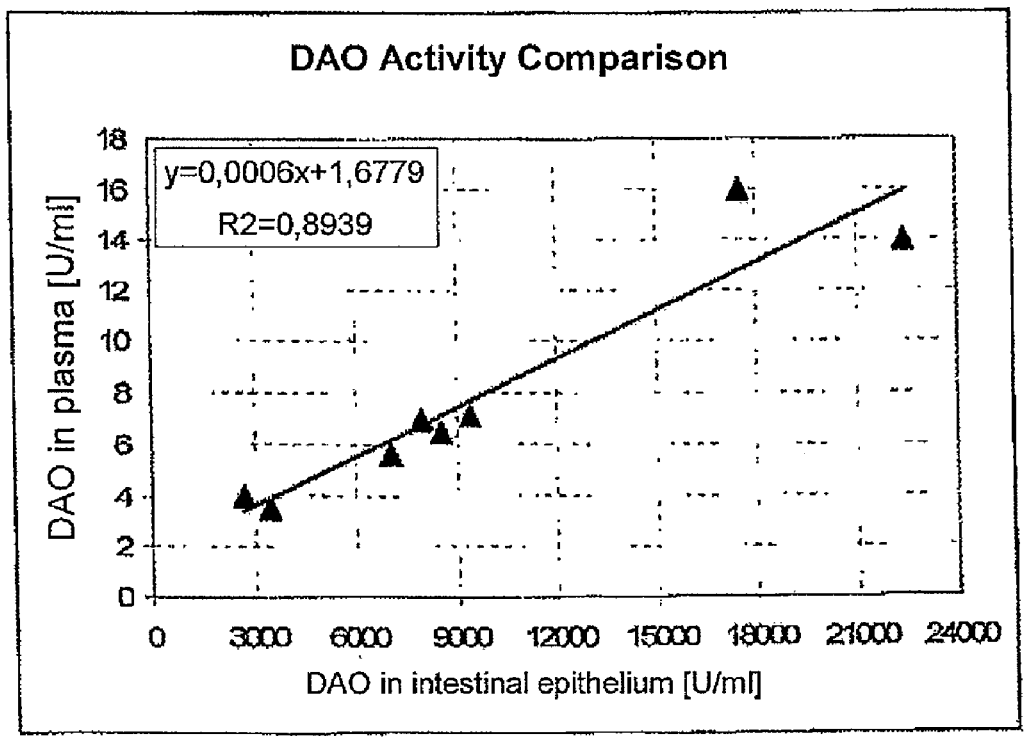

FIG. 8 shows the correlation between the DAO activity in plasma and in the intestinal epithelium.

EXAMPLES

Example 1

Freshly taken samples (plasma or serum) were stored at 4° C. after having been taken. The samples can be stored up to 2 days at 4° C., and for extended periods at −20° C.

Day 1:

Standards were dissolved in 1.0 ml aqua deion. for 15 min at room temperature and mixed well (vortex).

On the batch protocol supplied, the positions for standards and samples were marked.

200 μl each of the standard and of the sample were pipetted into the respective wells of the incubation plate (preparation: mixing of 0.6 μl histamine (1 mg/ml in 50 mM Tris pH 8), 0.2 μl catalase, crystal suspension in water, 0.12 g sucrose, 120 μl 1M Tris, 2.3 ml RO water and pipetting 25 μl into each well).

Tapes were covered and incubated over night at room temperature (18-26° C.). Unused tapes were stored at 4° C. in aluminum bag with desiccant bag.

Day 2:

10× washing buffer concentrate was diluted 1+9 with aqua deion. (e.g. 60 ml washing buffer concentrate plus 540 ml aqua deion.) (final concentration: 100 mM Tris-HCl pH=9.0).

Acylation reagent (biotin NHS lyophilized; several vials according to demand) was dissolved (1 ml per vial) with aclyation diluent (DMSO (dimethylsulfoxide)+DMFO (dimethylformamide) 1:1), optionally pooled, mixed well. The dissolved reagent should be used within 30 minutes.

50 μl of the dissolved acylation reagent was pipetted into each well of the incubation plate along with sample (e.g. by multipipette). Unused tapes were stored at 4° C. in aluminum bag with desiccant bag.

Tapes were incubated on shaker at 37° C. for 30 min.

150 μl assay buffer (50 mM Tris pH 8, 100 mM NaCl, 2% PEG) was pipetted into the required wells of the enhancer plate (preparation: providing 24 ml antibody buffer (50 mM Tris pH 8, 100 mM NaCl, 2% PEG, 5% sucrose, adding 19 μl serum anti-acyl histamine (e.g. goat serum) and mixing and pipetting into each well).

50 μl sample from the incubation plate was transferred into the respective wells of the enhancer plate (multichannel pipette). Unused tapes were stored at 4° C. in aluminum bag with desiccant bag.

Tapes were covered and incubated on shaker at 37° C. for 45 min.

150 μl reaction mixture from the enhancer plate was transferred into the respective wells of the ELISA plate (multi-channel pipette). Unused tapes were stored at 4° C. in aluminum bag with desiccant bag.

Tapes were covered and incubated on shaker at 37° C. for 90 min.

The contents of the wells was discarded and the wells were washed 4 times with 350 μl of diluted washing buffer.

100 μl conjugate (e.g., rabbit anti-goat-HRPO 1:5000 on PO stabilizer; manufactured by e-bioscience) was pipetted into all wells.

Tapes were covered and incubated on shaker at 37° C. for 30 min.

The contents of the wells was discarded and the wells were washed 4 times with 350 μl diluted washing buffer.

100 μl substrate (TMB (tetramethylbenzidine) ready for use, from Sigma) was pipetted into all wells and incubated at RT (18-26° C.) for 15 min.

50 μl stop solution (1M HCl) was pipetted into all wells.

The optical density was determined in an ELISA reader at 450 nm (reference: 620 nm).

Example 2

Figure 1:
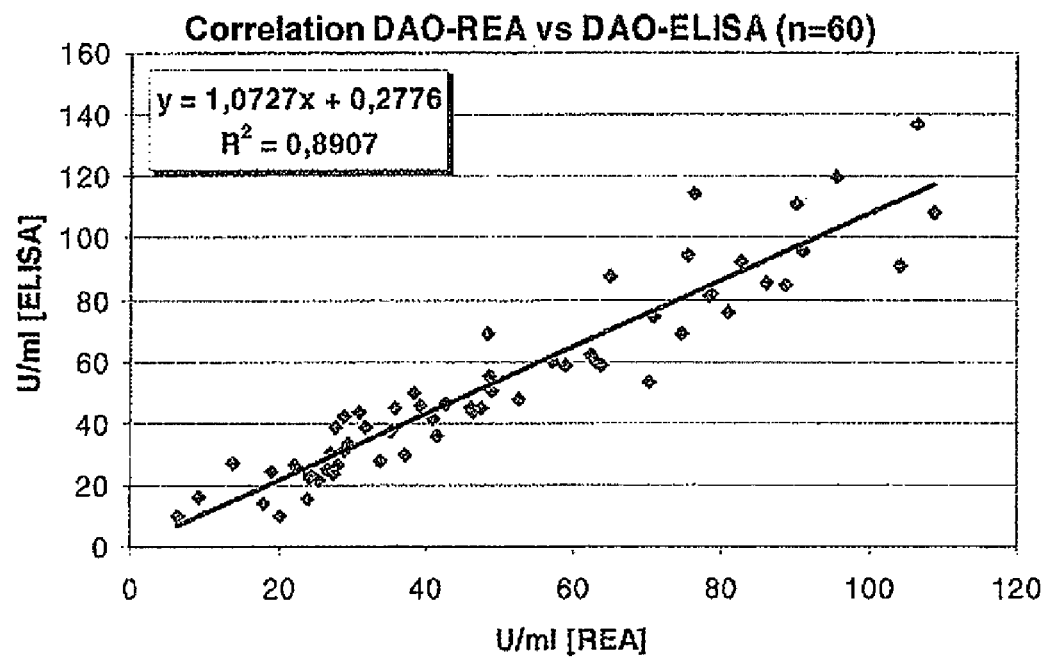
FIG. 1 shows the correlation of the measuring results from the determination of the enzymatic activity in a sample with a defined amount of DAO between the method according to the invention and a method using radioactively labelled diamine (AT 411.688).
Figure 2:
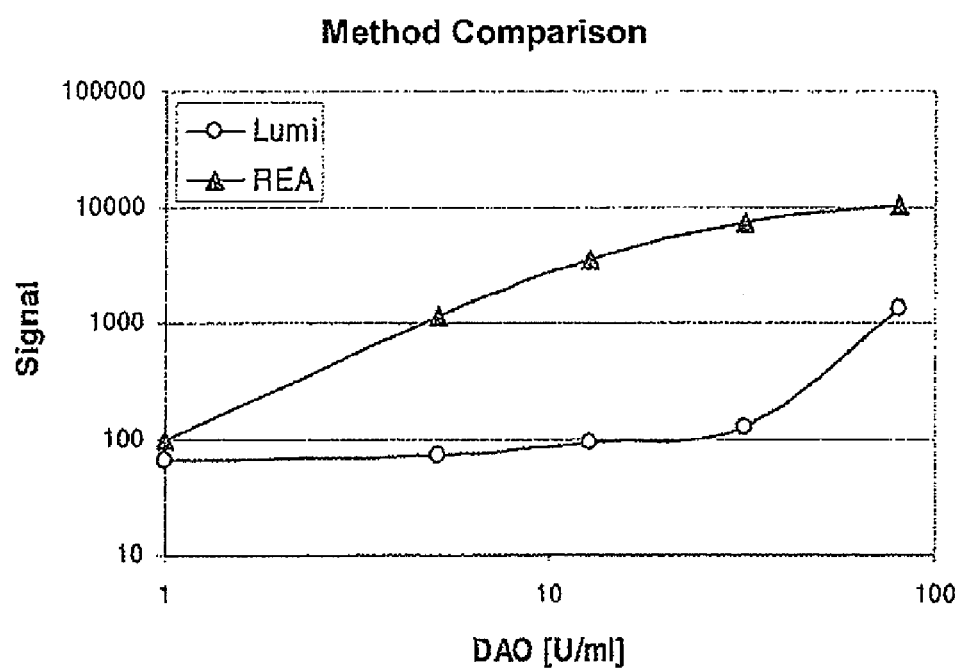
FIG. 2 illustrates a sensitivity comparison between a method for determining DAO activity in a sample using radioactively labelled diamine and a method for detecting hydrogen peroxide formed during the degradation of diamine by DAO.
Figure 3:
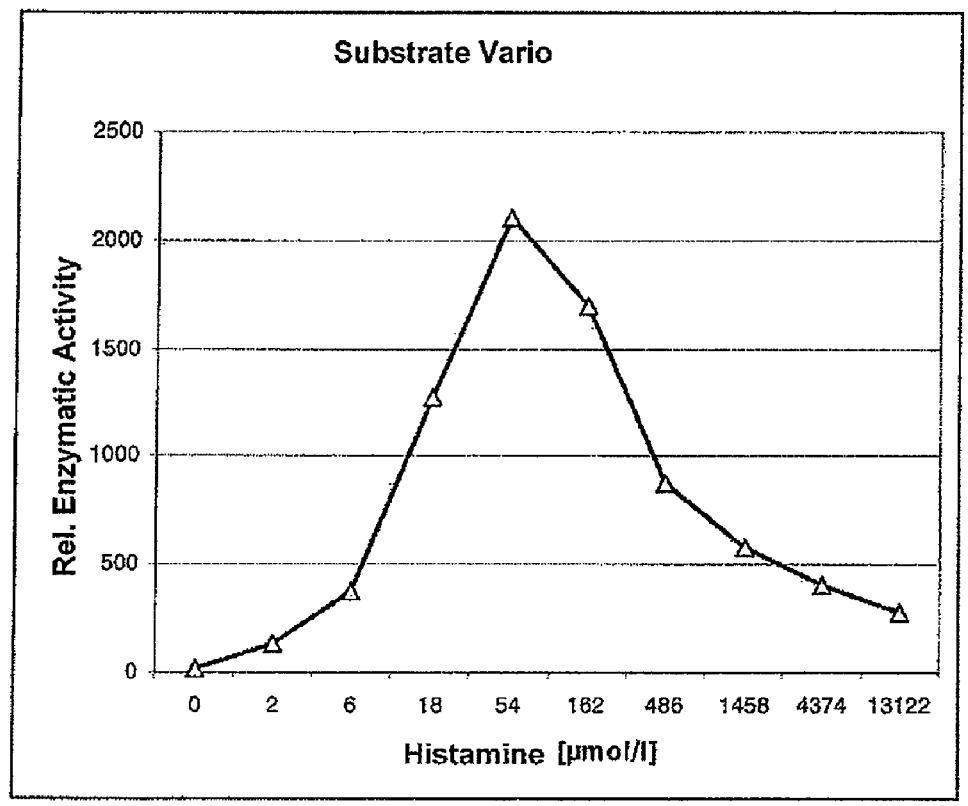
FIG. 3 depicts the relative enzymatic activity of a defined amount of DAO in a sample as a function of the amount of histamine used.
Figure 4:
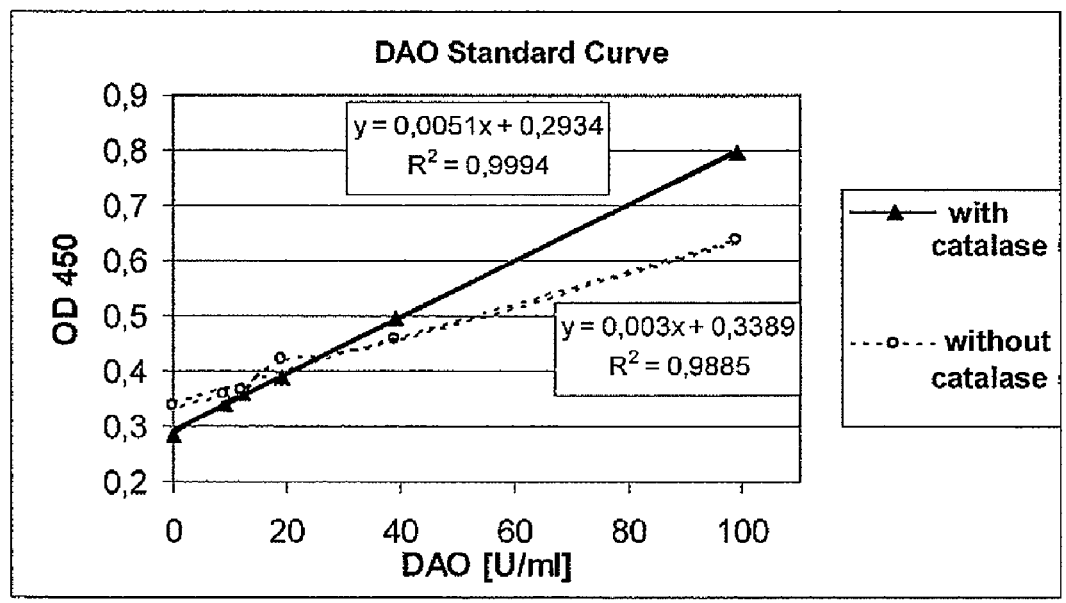
FIG. 4 shows a comparison of DAO standard curves with and without the addition of catalase.

In order to prevent the inhibition of DAO by hydrogen peroxide, the sample was admixed with catalase. This caused a significant improvement in the slope, and a substantially enhanced linearity, of the standard curve (cf. FIG. 4).

The catalase was admixed to the sample immediately before the reaction of DAO with histamine, the activity was 2 enzymatic units of catalase per 200 μl sample. In particular, the catalase was charged into the incubation plate lyophilized and along with histamine.

Example 3

The degradation of histamine is known to preferably occur by DAO in the intestinal lumen and in the intestinal epithelial cells. A comparison of the activity of DAO in plasma and in intestinal epithelial cells demonstrates the correlation postulated so far. Furthermore, it is noted that the activity of DAO in the intestinal epithelial cells is by a multiple (by a factor of about 100) larger than in blood.

10 mg biopsy material was homogenized in 50 mM Tris buffer (pH=8.5+100 mM NaCl). The homogenate was diluted 1:300 in the buffer to bring it into the measurable range. This dilution was measured in the test analogously to the plasma sample.

In FIG. 8, the results of the DAO activity comparison are graphically represented.

Example 4

Example 4 uses the same samples as Example 1. Example 4 is another way of realizing the method according to the invention.

Day 1:

1. Dissolve standards in 1 ml assay reagent (water with preservants); allow to dissolve at RT for 15 min, mix well (vortex). Nonrequired standards may be stored up to 3 days at 4° C., extended storage until expiry date at −20° C.

2. Dissolve control in 1 ml assay reagent; allow to dissolve at RT for 15 min, mix well (vortex). Nonrequired standards may be stored up to 3 days at 4° C., extended storage until expiry date at −20° C.

3. Mark positions for standards, control and samples in batch protocol.

Remove required tapes of incubation plate from bag (preparation: mix 0.6 μl histamine (mixing 1 mg/ml in 50 mM Tris pH 8), 0.2 μl catalase, crystal suspension in water, 0.12 g sucrose, 120 μl 1M Tris, 2.3 ml RO water and pipette 25 μl into each well, lyophilize).

Store unused tapes at 4° C. in aluminum bag with desiccant bag.

4. Pipette 50 μl each of the standard, control and sample into the respective wells of incubation plate.

5. Pipette 50 μl assay reagent into all wells, shake slightly.

6. Cover tapes and incubate over night at 37° C. (under shaking, if possible).

Day 2:

7. Dilute 10× washing buffer concentration with aqua deion. 1+9 (e.g., 60 ml washing buffer concentrate plus 540 ml aqua deion.; final concentration: 100 mM Tris-HCl pH=9.0+0.05% Bridge 35).

The diluted washing buffer concentrate is storable at 4° C.

8. Dissolve antibodies (e.g., goat anti-histamine derivative) in 20 ml assay buffer (50 mM Tris pH=8.05+100 mM NaCl).

9. Dissolve acylation reagent (biotin-NHS lyophilized; several vials according to demand) with acylation dilutant (DMSO (dimethylsulfoxide)+DMFO (dimethylformamide) 1:1) (1 ml per vial), optionally pool, mix well. The dissolved reagent should be used within 30 min.

10. Pipette 20 μl of the dissolved acylation reagent into each well of the incubation plate along with sample.

11. Incubate tapes at 37° C. for 30 min (optionally under careful shaking), DO NOT cover!

12. Pipette 150 μl assay reagent into each well.

13. Incubate tapes at 37° C. for 30 min (optionally under careful shaking), DO NOT cover!

14. Remove required tapes of ELISA plate (coated with derivatized diamine) from bag.

Store unused tapes at 4° C. in aluminum bag with desiccant bag.

15. Transfer 30 μl sample from incubation plate into the respective wells of ELISA plate.

16. Pipette 150 μl of dissolved antibody solution (cf. point 8) into the respective wells of ELISA plate.

17. Cover tapes and incubate at 37° C. for 45 min (optionally under shaking).

18. Discard contents of wells and wash 4 times with 300 μl diluted washing buffer.

19. Pipette 100 μl conjugate (e.g., rabbit anti-goat HRPO) into all wells.

20. Cover tapes and incubate at 37° C. for 30 min (optionally under shaking)

21. Discard contents of wells and wash 4 times with 350 μl diluted washing buffer.

22. Pipette 100 μl substrate (e.g. tetramethylbenzidine/hydrogen peroxide mixture) into all wells.

23. Incubate at RT (18-26° C.) for 15 min.

24. Pipette 50 μl stop solution (e.g. 1M HCl) into all wells.

25. Determine optical density in an ELISA reader at 450 nm (reference: 620 nm).

The invention claimed is:

1. A method for determining diamine oxidase (DAO) activity in a sample comprising:
   providing a known amount of a diamine admixed with the sample;
   incubating the diamine under conditions at which the diamine would react with any present DAO in the sample;
   derivatizing diamine present after the incubation;
   determining an amount of any derivatized diamine; and
   comparing the known amount of diamine with the amount of derivatized diamine to determine the amount of diamine that was degraded; and
   determining the DAO activity based on the amount of degraded diamine.

2. The method of claim 1, wherein the diamine is in an aqueous solution or lyophilized.

3. The method of claim 1, further comprising:
   incubating with the diamine and the diamine oxidase a compound potentially inhibiting the activity of diamine oxidase, for a fixed period under conditions at which the diamine can be reacted by a DAO possibly present in the sample;
   derivatizing diamine present after the incubation;
   determining an amount of derivatized diamine, if any;
   comparing the known amount of diamine with the amount of derivatized diamine to determine the activity of the diamine oxidase in the presence of the potentially inhibiting compound; and
   comparing the activity of the diamine oxidase with the potentially inhibiting compound with the activity of the diamine oxidase without the potentially inhibiting compound, wherein the potentially inhibiting compound is determined to be a diamine oxidase inhibitor if is lowers the activity of the diamine oxidase by at least 20%.

4. The method of claim 1, wherein the diamine is histamine, putrescine, spermidine, and/or cadaverine.

5. The method of claim 1, wherein the aqueous solution comprises a Tris (Tris(hydroxymethyl)-aminomethane) buffer solution having a pH of 7 to 9.5.

6. The method of claim 1, wherein the aqueous solution contains a diamine in an amount of from 5 to 400 μM.

7. The method of claim 1, wherein the incubation of the aqueous solution with the sample takes place at a temperature of from 10 to 50° C.

8. The method of claim 1, wherein the incubation of the aqueous solution with the sample is effected for 30 minutes to 36 hours.

9. The method of claim 1, wherein incubation of an aqueous solution with the sample is stopped before derivatizing with amino guanidine.

10. The method of claim 1, wherein derivatizing the diamine comprises acylating.

11. The method of claim 10, wherein the diamine is acylated with NHS biotin.

12. The method of claim 1, wherein the amount of derivatized diamine is determined by chromatography, electrophoresis, or immunoassay.

13. The method of claim 12, wherein the amount of derivatized diamine is determined by high-performance liquid chromatography (HPLC), capillary electrophoresis (CE), enzyme-linked immunosorbent assay (ELISA), or radioimmunoassay (RIA).

14. The method of claim 2, wherein peroxidase is admixed with the aqueous solution and/or the sample.

15. The method of claim 14, wherein the peroxidase is catalase.

16. The method of claim 14, wherein the peroxidase is admixed in an amount of from 0.1 to 10 unit(s) of peroxidase per 100 μl sample.

17. The method of claim 16, wherein the peroxidase is admixed in an amount of 1 unit of peroxidase per 100 μl sample.

* * * * *